US010159449B2

(12) United States Patent
Shang (10) Patent No.: US 10,159,449 B2
(45) Date of Patent: Dec. 25, 2018

(54) BED BOARD COMPOSED OF BASALT FIBERS FOR A DIAGNOSTIC BED OF A MEDICAL APPARATUS, AND METHOD FOR MANUFACTURING A BED BOARD

(71) Applicant: Siemens Healthcare GmbH, Erlangen (DE)

(72) Inventor: Hong Shang, Shanghai (CN)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/643,645

(22) Filed: Jul. 7, 2017

(65) Prior Publication Data
US 2018/0008211 A1    Jan. 11, 2018

(30) Foreign Application Priority Data

Jul. 7, 2016    (CN) .......................... 2016 1 0529269

(51) Int. Cl.
| | | |
|---|---|---|
| *A61B 6/00* | (2006.01) | |
| *A61B 6/04* | (2006.01) | |
| *A61B 5/055* | (2006.01) | |
| *A61B 5/00* | (2006.01) | |
| *B29C 70/44* | (2006.01) | |
| *B29C 70/46* | (2006.01) | |
| *B29K 105/06* | (2006.01) | |
| *B29K 309/02* | (2006.01) | |
| *B29L 31/00* | (2006.01) | |

(52) U.S. Cl.
CPC .......... *A61B 6/0442* (2013.01); *A61B 5/0555* (2013.01); *A61B 5/704* (2013.01); *A61B 6/0407* (2013.01); *A61B 6/0457* (2013.01); *B29C 70/443* (2013.01); *B29C 70/46* (2013.01); *A61B 2562/12* (2013.01); *B29K 2105/06* (2013.01); *B29K 2309/02* (2013.01); *B29K 2905/00* (2013.01); *B29L 2031/753* (2013.01)

(58) Field of Classification Search
CPC ....................................................... A61B 6/00
USPC ..................................................... 5/601, 600
See application file for complete search history.

(56) References Cited

U.S. PATENT DOCUMENTS

| | | | | |
|---|---|---|---|---|
| 3,947,686 | A * | 3/1976 | Cooper ................ | A61B 6/0442 378/209 |
| 4,312,912 | A | 1/1982 | Tamura | |
| 5,210,893 | A * | 5/1993 | Uosaki ................ | A61B 5/0555 5/600 |
| 9,179,880 | B2 | 11/2015 | Coppens et al. | |
| 2013/0305452 | A1 | 11/2013 | Zhongqiang et al. | |
| 2016/0299085 | A1* | 10/2016 | Fisset ..................... | G01N 29/11 |

OTHER PUBLICATIONS

Jamshaid, "Basalt Fiber and Its Applications," Journal of Textile Engineering and Fashion Technology, vol. 1, No. 6 (2017).
Dhand et al., "A Short Review on Basalt Fiber Reinforced Polymer Composites," Composites Part B, vol. 73, pp. 166-180 (2014).

* cited by examiner

*Primary Examiner* — Frederick C Conley
(74) *Attorney, Agent, or Firm* — Schiff Hardin LLP (57) ABSTRACT

A bed board for a diagnostic bed of a medical examination apparatus is formed in a material that includes basalt fibers. The bed board may have a bed board body composed of basalt fibers and a filler in a predetermined ratio, or may be formed by a hollow shell, composed of basalt fibers and a binder in a predetermined ratio, with the hollow shell being filled by a filler material.

2 Claims, 10 Drawing Sheets

BED BOARD COMPOSED OF BASALT FIBERS FOR A DIAGNOSTIC BED OF A MEDICAL APPARATUS, AND METHOD FOR MANUFACTURING A BED BOARD

BACKGROUND OF THE INVENTION

Field of the Invention

The present invention relates to the field of medical apparatus manufacturing, in particular to manufacturing a bed board for a medical imaging apparatus, and a diagnostic bed, a medical apparatus and a method for manufacturing a bed board.

Description of the Prior Art

Large medical apparatuses, such as computed tomography (CT) systems, magnetic resonance (MR) systems and large C-arm (angiography) systems, are basically composed of a data acquisition scanner and a diagnostic bed.

In a large medical imaging apparatus, due to penetrating radiation and magnetic fields being involved in the modality that is used, a bed board of the diagnostic bed must be able to adapt to a corresponding medical environment, interference to medical detection results must be reduced to a very low level, and at the same time, the bed board must have a certain strength, so as to be able to safely bear an examination subject. The choice of material for such a bed board for a medical imaging apparatus thus is a very important technical problem.

At present, carbon fiber and fiberglass are the principal materials used for bed components. In particular, CT bed boards and bed boards for C-arm beds require load-bearing capability and rigidity, and the requirements in relation to aluminium equivalent and X-ray absorption, etc. are stringent, and have a direct impact on diagnosis results. Therefore, the requirements placed on materials are strict. Among several major fiber materials, carbon fiber material has the best overall performance, and is also the only material that can be used for an X-ray bed board; there is no substitute for it. It is the most expensive composite material, but meets the requirements of clinical tests.

The diagnostic bed of a CT apparatus is one of the important constituent parts of the CT apparatus. The bed board design of the diagnostic bed plays a key role in patient safety and image quality; the quality of an image is directly related to the choice of bed board material. At present, carbon fiber combined with a filler is employed as a material in such a diagnostic bed. Carbon fiber material has advantages such as high strength, good rigidity, low ray absorption, low CT value, low image noise, and low aluminium equivalent.

MR (magnetic resonance) imaging places even more stringent requirements on the materials used in the MR apparatus. The materials must be anti-magnetic, and electrically insulating. Only non-metallic materials satisfy such conditions. ABS/PC/fiberglass all meet the requirements, but the performance indices and overall performance of ABS/PC are inferior to those of fiberglass. Therefore only fiberglass composite material is suitable for MR bed board manufacture. Such material also satisfies load-bearing and imaging requirements for MR examinations. Thus, bed boards of existing MR diagnostic beds use fiberglass as a material, thereby attaining load-bearing and anti-magnetic functions, and also meeting image quality requirements.

C-arm (angiography) bed boards have certain features in common with CT bed boards, but the requirements in relation to overall rigidity are more stringent. Therefore, carbon fiber material is also the first choice for C-arm bed boards. The requirements placed on the bed boards of existing C-arm diagnostic beds in relation to image quality and load-bearing are also very stringent. At present, they are composed of carbon fiber material in combination with a filler, and have advantages such as good rigidity, low ray absorption, low CT value, low image noise, and low aluminium equivalent.

However, the cost of conventional materials used for bed boards for existing medical apparatuses is generally high.

SUMMARY OF THE INVENTION

An object of the present invention is to provide a bed board and a diagnostic bed, a medical apparatus, and a bed board manufacturing method, using a material for the bed board that reduces costs while meeting medical apparatus imaging requirements.

A bed board in accordance with the invention for a diagnostic bed has a shape and dimensions so as to fit within a bed frame of a supporting device, which supports the bed board, and wherein the bed board is driven within the frame by a driving device so as to move the bed board relative to the bed frame. The material of the bed board includes basalt fibers.

In a preferred embodiment of the bed board, the bed board is formed by binding basalt fibers with a binder in a specified ratio.

In a preferred embodiment of the bed board, the bed board has a shell and a lightweight filler. The shell is made by binding basalt fibers with a binder in a specified ratio. The interior of the shell is hollow, and filled with the lightweight filler.

A diagnostic bed in accordance with the invention includes the bed board, and the supporting device and frame, and the driving device.

A medical imaging apparatus in accordance with the invention includes the diagnostic bed, and an image data acquisition scanner in which the bed board is moveable.

A method for manufacturing a bed board in accordance with the invention includes forming the bed board from basalt fibers and a binder in a specified ratio, by manual pasting, or by metal mold pressing, or by vacuum infusion low-pressure forming.

In an embodiment of the inventive method for manufacturing a bed board, wherein the forming is by manual pasting, then the ratio of the basalt fibers to the binder is 1:1.

In an embodiment of the inventive method for manufacturing a bed board, wherein the forming is by metal mold pressing, then the ratio of the basalt fibers to the binder is 7:3.

In an embodiment of the inventive method for manufacturing a bed board, wherein the forming is by vacuum infusion low-pressure forming, then when the pressure is lower than a specified pressure, the ratio of the basalt fibers to the binder is 6:4. When the pressure is increased, the proportion of the basalt fibers also synchronously increases by a specified value.

Another method for manufacturing a bed board in accordance with the invention includes using basalt fibers and an adhesive in a specified ratio to make a shell, using the shell to enclose a filler, and then forming the bed board. The filler is selected from the group consisting of wood-based material, foamed material and plastic.

In embodiments of the present invention, basalt fibers are used to manufacture a component for a medical imaging apparatus. Not only does such a basalt fiber component have a low-cost, but also noise interference to medical apparatus scan imaging will be vastly reduced, such that the quality of medical apparatus scan imaging is greatly improved.

At the same time, the bed board for a medical apparatus according to the present invention has characteristics such as a high tensile strength, and is anti-magnetic, electrically insulating, environmentally friendly, resistant to acids, alkalis and high temperatures, and is made by a simple manufacturing process. The use of the basalt fibers solves the problem of a lack of variety of diagnostic bed board materials in medical imaging apparatuses, thereby enlarging the range of materials that may be chosen, while improving the image quality of the medical apparatus, improving the overall performance indices, and lowering costs. When basalt fibers are used to manufacture a bed board for a medical imaging apparatus, not only do the strength and load-bearing capability of the bed board meet requirements, but also the thickness is smaller, and imaging quality is better.

Due to the characteristics of basalt fibers, such as being low-cost, environmentally friendly, easy to manufacture, acid-resistant, alkali-resistant, high temperature resistant, anti-magnetic and electrically insulating, besides being able to be used in a bed board of a medical apparatus, in particular a medical imaging apparatus, such material may also be used in other components of a medical apparatus, e.g. an outer cover (housing shell) or load-bearing component of a medical imaging apparatus.

BRIEF DESCRIPTION OF THE DRAWINGS

FIG. 6b is another perspective view of the diagnostic bed shown in FIG. 6a.

FIG. 6c is a sectional view of the diagnostic bed shown in FIG. 6a.

FIG. 7b is a perspective view of the diagnostic bed shown in FIG. 7a.

DESCRIPTION OF THE PREFERRED EMBODIMENTS

The present invention is explained in detail below in conjunction with the accompanying drawings, with regard to the technical solution and advantages thereof. It should be understood that the particular embodiments described herein are only intended as examples to explain the present invention.

The principal technical solution of the present invention is a component for a medical apparatus, the material of the member including basalt fibers.

The medical apparatus according to the present invention may be any of an MR apparatus, a CT apparatus, an angiography apparatus, an X-ray apparatus, etc.

Figure 1:
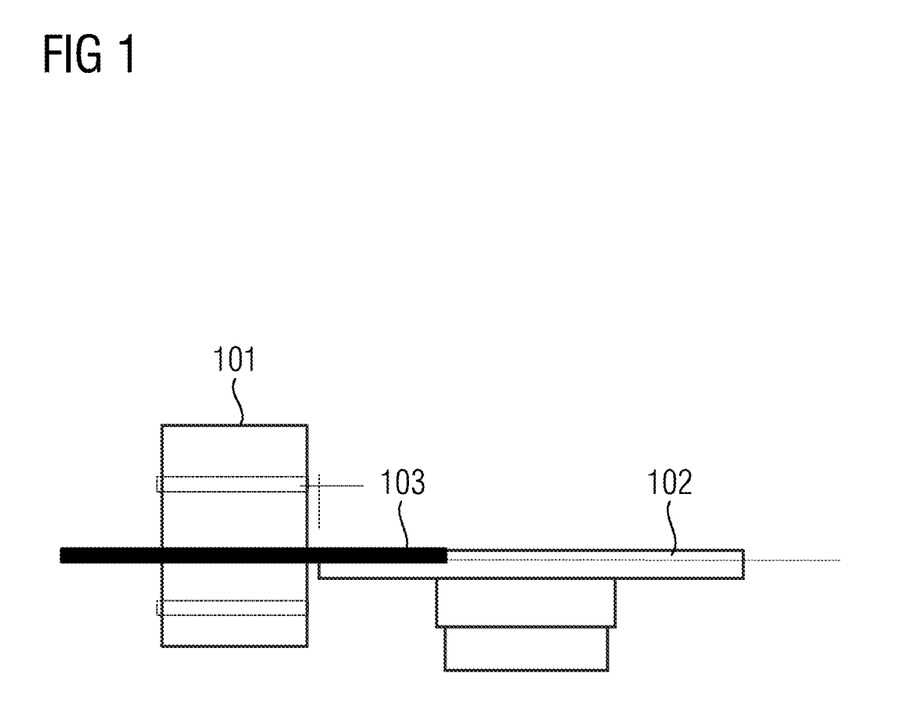
FIG. 1 is a schematic illustration of an MR detection apparatus.

As an example, FIG. 1 schematically illustrates an MR detection apparatus. The MR detection apparatus has an MR data acquisition scanner 101, an MR table 102 and an MR bed board (table top) 103.

Figure 2:
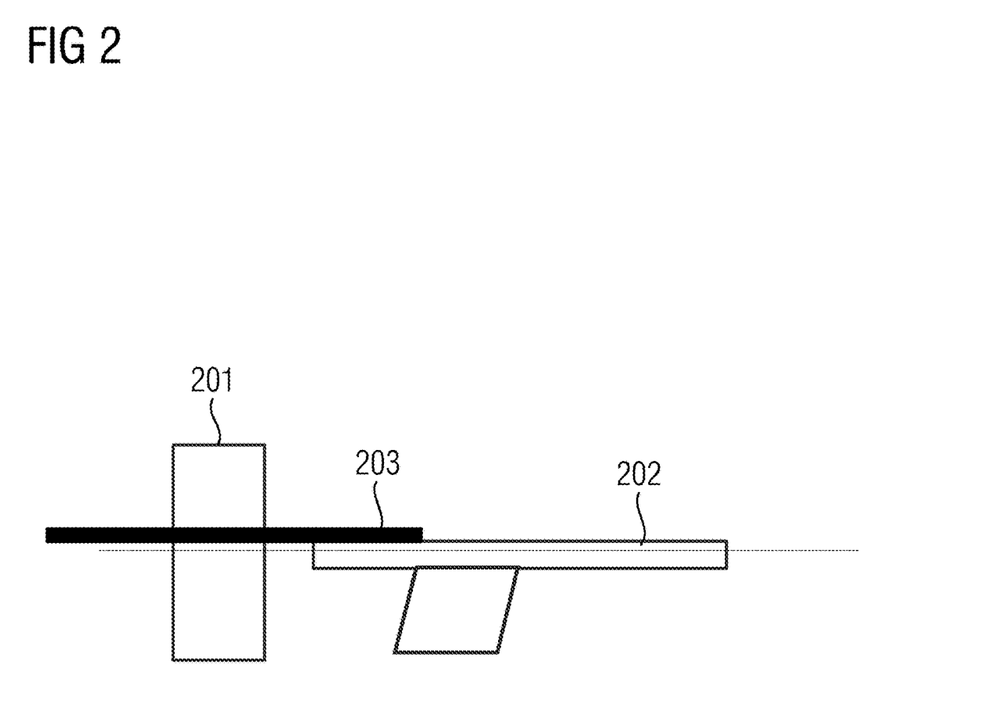
FIG. 2 is a schematic illustration of a CT apparatus.

FIG. 2 schematically illustrates a CT apparatus having a CT gantry 201, a CT table 202, and a CT bed board 203.

Figure 3:
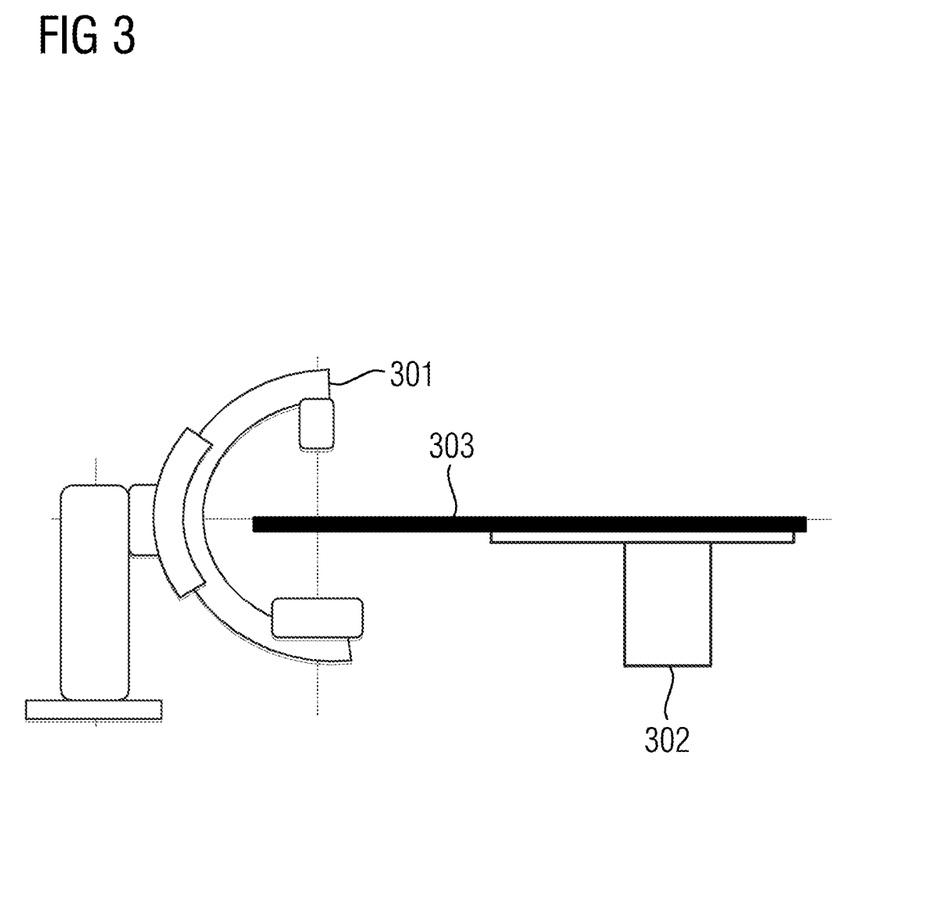
FIG. 3 is a schematic illustration of a C-arm angiography apparatus.

FIG. 3 schematically illustrates an angiography apparatus; that has an imaging device 301, an imaging table (cam table) 302, and a C-arm bed board 303.

In a preferred embodiment, the component of a medical apparatus according to the present invention is a bed board for a diagnostic bed of a medical imaging apparatus, such as the MR bed board 103 in FIG. 1, the CT bed board 203 in FIG. 2, and the C-arm bed board 303 in FIG. 3.

However, in addition to a bed board which may be used in a medical apparatus, in particular a medical imaging apparatus, the medical apparatus component according to the present invention may be other components of a medical apparatus, e.g. a table or bed frame for bearing the bed board in a medical imaging apparatus, a supporting shaft arm, or even an outer cover or load-bearing component of the medical apparatus; the member for a medical apparatus according to the present invention may also replace an aluminium profile in the medical apparatus.

The present invention also encompasses a medical imaging apparatus, and a diagnostic bed for a medical apparatus, which include the bed board according to the present invention.

The bed board according to the present invention has a size and shape so as to fit within a frame of a supporting device, which supports the bed board, and wherein the bed board is driven by a driving device, which moved the bed board relative to the bed frame. The material of the bed board includes basalt fibers.

The medical apparatus according to the present invention may be an MR diagnostic apparatus, a CT diagnostic apparatus, an EAS cardiovascular diagnostic apparatus, etc. An example is given below to explain the structure of the diagnostic bed of a medical apparatus according to the present invention.

Figure 6A:
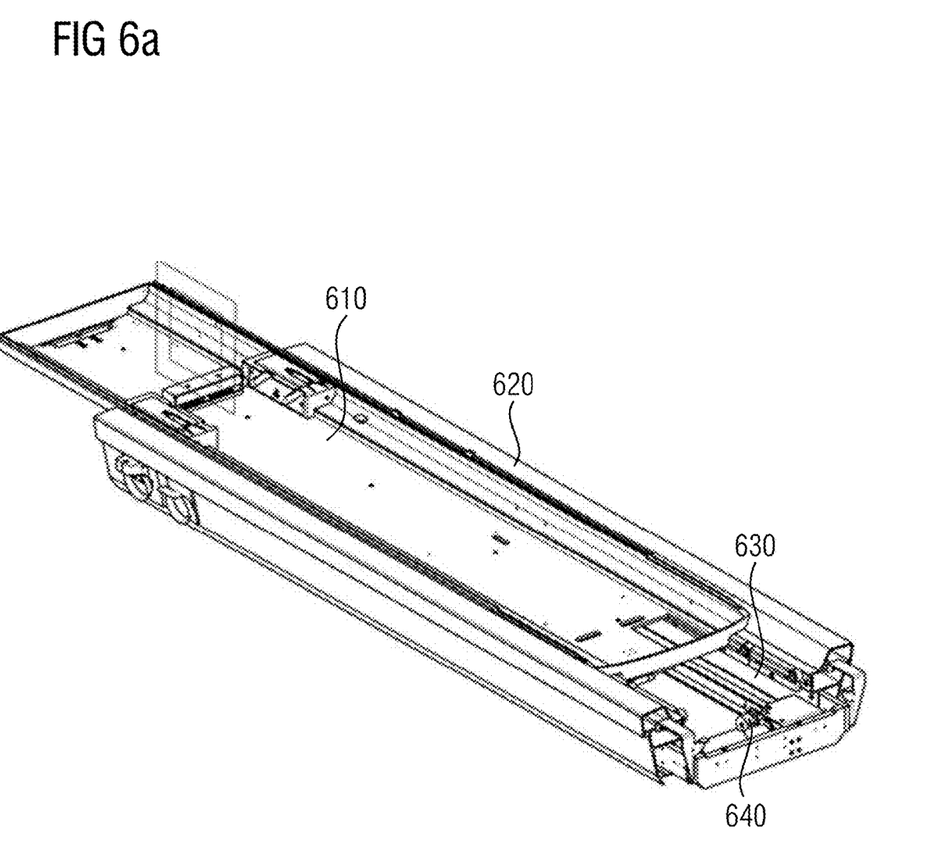
FIG. 6a is a perspective view of a diagnostic bed in an MR diagnostic apparatus according to the present invention.
Figure 6B:
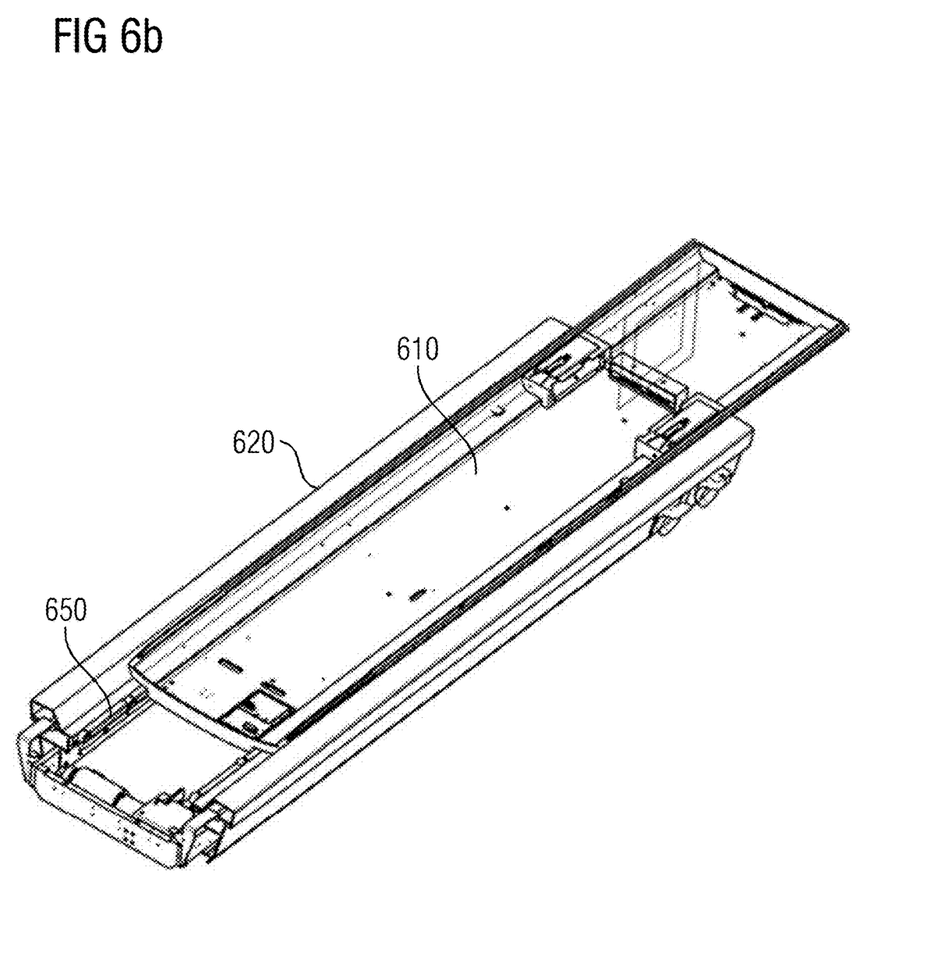
Figure 6C:
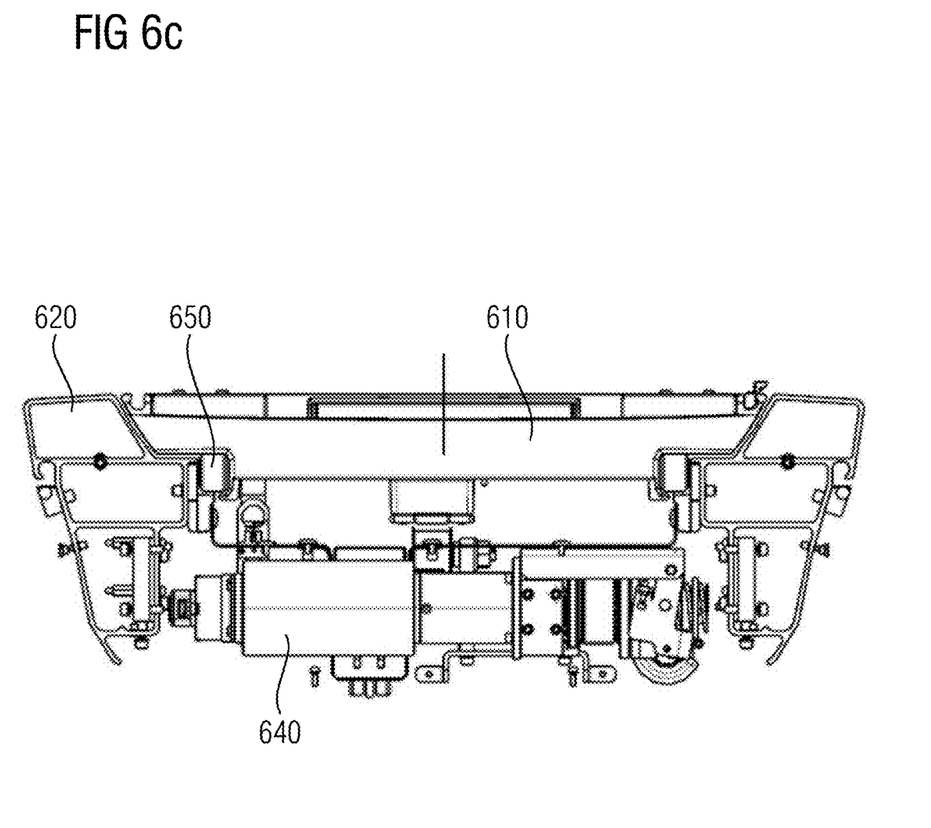

FIG. 6a is a perspective view of a diagnostic bed in an MR diagnostic apparatus according to the present invention; FIG. 6b is another perspective view of the diagnostic bed shown in FIG. 6a; FIG. 6c is a sectional view of the diagnostic bed shown in FIG. 6a. As FIGS. 6a, 6b and 6c show, the diagnostic bed has a bed board 610, a bed frame 620, a supporting device 650 and a driving device; the driving device being a synchronous belt 630 and a drive motor assembly 640. The material of the bed board 610 includes basalt fibers. The supporting device 650 is disposed on the bed frame 620, and is supported by the bed frame 620. The supporting device 650 is a support wheel assembly, with the bed board 610 being placed on the support wheel assembly 650 and so as to be moveable horizontally. The drive motor assembly 640 of the driving device drives the synchronous belt 630, and the synchronous belt 630 is connected to the bed board 610, so that the driven horizontal movement of the synchronous belt 630 causes synchronous horizontal movement of the bed board 610 on the support wheel assembly 650.

Figure 7A:
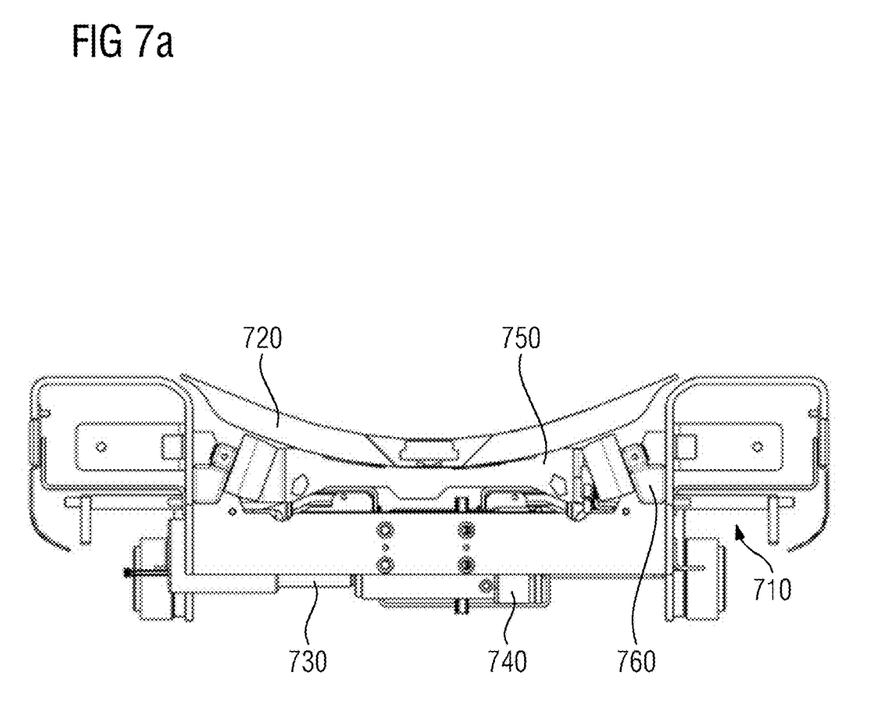
FIG. 7a is a sectional view of a diagnostic bed in a CT diagnostic apparatus according to the present invention.
Figure 7B:
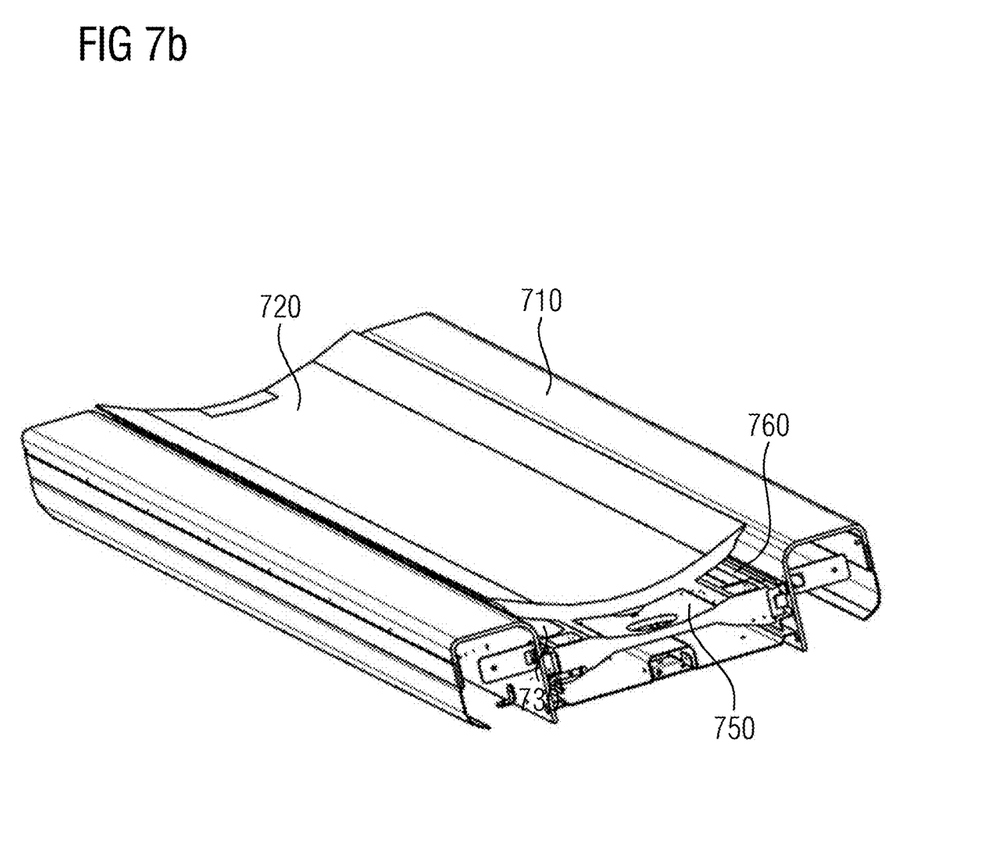

FIG. 7a is a sectional view of a diagnostic bed in a CT diagnostic apparatus according to the present invention; FIG. 7b is a perspective view of the diagnostic bed shown in FIG. 7a. Referring to FIGS. 7a and 7b, the diagnostic bed comprises a bed frame 710, a bed board 720, a trailer (i.e. supporting device) 750 and a horizontal drive assembly (i.e. driving device) 730. The material of the bed board 720 includes basalt fibers. The trailer 750 is disposed on the bed frame 710, and is supported by the bed frame 710. The bed board 720 is disposed on the trailer 750, and is supported by the trailer 750. A linear guide rail 760 is also provided on the bed frame 710. The horizontal drive assembly 730 drives the trailer 750 so as to move along the linear guide rail 760, thereby causing the bed board 720 to move along the path of the linear guide rail 760. The diagnostic bed may further have a brake 740 that imparts a braking force to the bed board 720 or one of the components that moves the bed board 720.

In a preferred embodiment, the material of the member or bed board of the medical apparatus includes basalt fibers and a binder, and is formed by binding basalt fibers with binder in a specified ratio. Correspondingly, in one embodiment of the diagnostic bed for a medical apparatus, the bed board is formed by binding basalt fibers with a binder in a specified ratio.

Many choices are possible for the binder, for instance the binder may be an epoxy unsaturated resin, a modified unsaturated resin, vinyl groups or a PA binder, etc. Of course, the binder may also be a combination of two or more binders. In a preferred embodiment, the binder used is vinyl groups. Vinyl groups bind well with basalt fibers, so can increase the overall strength of the medical apparatus member or bed board.

In one embodiment of the present invention, the overall structure of the medical apparatus bed board may be formed by binding basalt fibers with a binder, according to the shape and structure of the medical apparatus bed board; with regard to a connection structure for the bed board and the medical apparatus, an existing connection structure may be retained.

Since a medical apparatus must have stringent requirements in relation to apparatus performance (e.g. precision of detection results), very stringent criteria are applied to the selection of material, and the choice of material for medical apparatuses is generally expensive. As a result, those skilled in the art tend to select medical apparatus member material from expensive materials with excellent properties.

Basalt fibers are very low-cost, and are mainly used in the field of fire prevention and fire resistance. However, it is impossible to know in advance what kind of technical effects could be achieved by using basalt fiber material in a medical apparatus, so those skilled in the art would not previously have thought of using basalt fiber material in a medical apparatus.

In the present invention, basalt fiber material is used in a medical apparatus, to make a member of the medical apparatus; in particular, the member may be a bed board of a medical apparatus diagnostic bed, and unforeseeable technical effects are achieved through experiment and application, including the following. Not only does such a basalt fiber member or bed board have excellent mechanical properties, but noise interference to medical apparatus scanning and imaging will be vastly reduced, greatly improving the quality of medical apparatus scanning and imaging. Experimental data and results are now disclosed as follows:

First set of experiments: the use of a basalt fiber bed board in an MR detection medical apparatus was compared with the use of a fiberglass bed board in an MR detection medical apparatus. The strength comparison experimental data produced and comparison experimental data obtained are shown in tables 1, 2 and 3:

TABLE 1

| test sample block | no. | width (mm) | thickness (mm) | area ($mm^2$) | max load (N) | bending strength (MPa) | elastic modulus (MPa) | support span (mm) |
|---|---|---|---|---|---|---|---|---|
| 4 mm thick basalt fiber bed board | 4-01 | 14.3 | 4.0 | 57.2 | 1055.0 | 484.2 | 21860.0 | 70.0 |
| | 4-02 | 13.2 | 4.0 | 52.8 | 1100.0 | 546.9 | 25115.0 | 70.0 |
| | 4-03 | 14.8 | 4.0 | 59.2 | 1195.0 | 529.9 | 24850.0 | 70.0 |
| | 4-04 | 15.0 | 4.0 | 60.0 | 1170.0 | 511.9 | 22485.0 | 70.0 |
| | 4-05 | 14.1 | 4.0 | 56.4 | 1205.0 | 560.8 | 23270.0 | 70.0 |
| mean | | 14.3 | 4.0 | 57.1 | 1145.0 | 526.7 | 23516.0 | 70.0 |

TABLE 2

| test sample block | no. | width (mm) | thickness (mm) | area ($mm^2$) | max loan (N) | bending strength (MPa) | elastic modulus (MPa) | support span (mm) |
|---|---|---|---|---|---|---|---|---|
| 6 mm thick basalt fiber bed board | 6-01 | 13.4 | 6.2 | 83.1 | 1770.0 | 525.7 | 30375.0 | 102.0 |
| | 6-02 | 12.6 | 6.3 | 79.4 | 1650.0 | 504.8 | 29255.0 | 102.0 |
| | 6-03 | 13.0 | 6.2 | 80.6 | 1815.0 | 555.7 | 31835.0 | 102.0 |
| | 6-04 | 12.5 | 6.2 | 77.5 | 1660.0 | 528.6 | 29295.0 | 102.0 |
| | 6-05 | 14.3 | 6.2 | 81.8 | 1763.0 | 529.8 | 30353.0 | 102.0 |
| mean | | 13.2 | 6.2 | 81.8 | 1763.0 | 529.8 | 30353.0 | 102.0 |

TABLE 3

| test sample block | no. | width (mm) | thickness (mm) | area (mm²) | max load (N) | bending strength (MPa) | elastic modulus (MPa) | support span (mm) |
|---|---|---|---|---|---|---|---|---|
| 8 mm | 8-01 | 13.7 | 7.4 | 101.4 | 1475.0 | 353.9 | 21585.0 | 120.0 |
| thick | 8-02 | 13.4 | 7.5 | 100.5 | 1580.0 | 377.3 | 20270.0 | 120.0 |
| fiberglass | 8-03 | 15.5 | 7.5 | 116.2 | 1525.0 | 314.8 | 20850.0 | 120.0 |
| bed | 8-04 | 14.1 | 7.5 | 105.8 | 1650.0 | 374.5 | 21190.0 | 120.0 |
| board | 8-05 | 13.6 | 7.4 | 100.6 | 1425.0 | 344.4 | 19125.0 | 120.0 |
| mean | | 14.1 | 7.5 | 104.9 | 1531.0 | 353.0 | 20604.0 | 120.0 |

The following conclusion may be drawn based on the experimental data in tables 1, 2 and 3: based on the data for maximum load at fracture, the 8 mm thick fiberglass bed board and the 6 mm thick basalt fiber bed board have the same strength. In other words, while able to achieve the same strength, the basalt fiber bed board is not only low-cost but also of smaller volume.

Second set of experiments: load-bearing test. A load of 4 times the conventional patient body weight is applied to a bed board made of basalt fibers according to the present invention (a load of 9200 N is applied); the test results fully satisfy load-bearing requirements.

Figure 4:
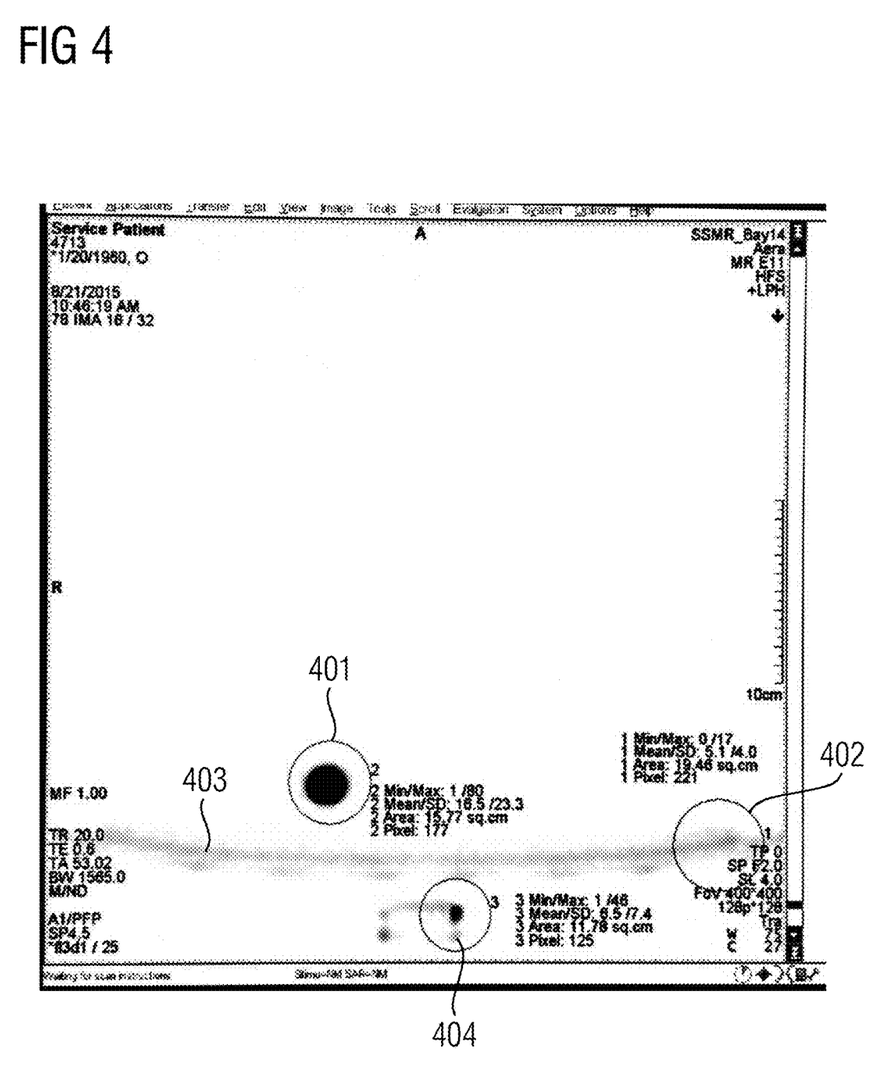
FIG. 4 shows results of comparative testing of the basalt fiber member of the present invention and comparison materials using an MR spine coil.

Third set of experiments: magnetic resonance (MR) spine coil imaging test. Specifically, an MR spine coil is used to test a sample of a large-area basalt fiber member according to the present invention. For comparison therewith, an ABS plastic member and a fiberglass member are used as comparison materials; at the same time, an MR spine coil is used to test the ABS plastic member and fiberglass member. FIG. 4 shows the results of this test, wherein the ABS plastic member is at the position of the round bar 401; as shown in the figure, the ABS plastic member has an obvious image, which will interfere with effective MR imaging. The fiberglass member is at the position of the round bar 402 and the curved, elongated shadow 403 on the left side thereof; the elongated shadow 403 shown in the figure is the image of the fiberglass member. This shadow can be clearly seen, and will therefore interfere with effective MR imaging. At the position of the round bar 404 is a fiberglass branch pipe, which will also produce an interference shadow which can be clearly seen. The basalt fiber member according to the present invention is at a middle position on the curved, elongated shadow 403 and the round bar 401. As the figure shows, at this position, a shadow of the basalt fiber member can hardly be seen. Thus, the basalt fiber member has much better non-imageability, with almost no image, and therefore causes very little interference to MR imaging, and meets the MR detection apparatus requirements.

Figure 5:
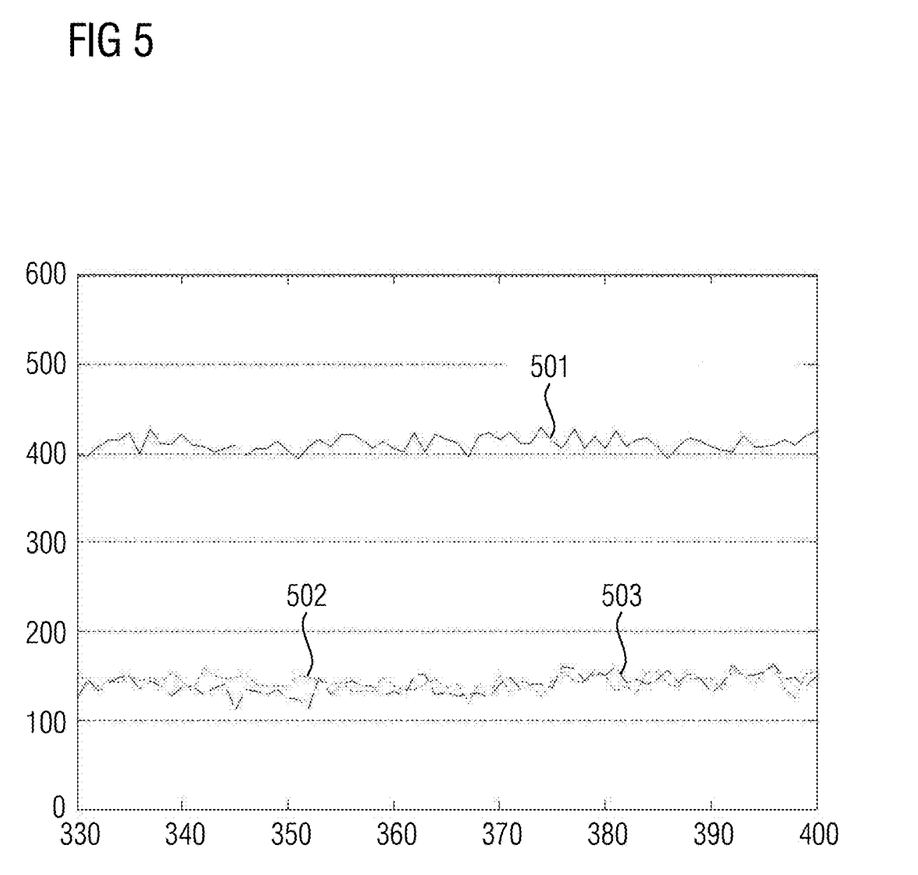
FIG. 5 is a graph of the results of a test comparing the absorption of penetrating radiation by the basalt fiber member of the present invention, and carbon fiber members.

Fourth set of experiments: measurement of medical apparatus ray absorption. FIG. 5 shows a graph of the results of a test comparing the absorption of medical apparatus rays by the basalt fiber member of the present invention and carbon fiber members. Referring to FIG. 5, the horizontal coordinates are channel numbers, while the vertical coordinates are residual ray values of rays that have undergone absorption. In this experiment, 130 kV, 120 mA rays are used, wherein curve 501 is a curve of residual ray values of rays that have undergone absorption in a basalt fiber member, and curves 502 and 503 are curves of residual ray values of identical rays that have undergone absorption in two different carbon fiber members respectively. As FIG. 5 shows, it is very obvious that the residual ray values of curve 501 are much higher than the residual ray values of curves 502 and 503, indicating that the absorption of medical apparatus rays by the basalt fiber member is much lower than absorption by the carbon fiber members, so the basalt fiber member is highly suitable for application in a medical apparatus member.

Correspondingly, the present invention also discloses a method for manufacturing a member for a medical apparatus, in particular a bed board. The method uses basalt fibers and a binder in a specified ratio to form the member or bed board.

The forming of the bed board may be implemented by any of the following embodiments.

First Embodiment: Forming by Manual Pasting

If the method of forming is forming by manual pasting, then the ratio of the basalt fibers to the binder is 1:1, or close to 1:1 within a specified tolerance. The term "specified tolerance" means that a specified error range may be set, e.g. within ±5%. The error range may be specified manually according to the application scenario of the medical apparatus member or bed board used.

Second Embodiment: Forming by Metal Mold Pressing

This method of processing has the advantage of high efficiency. If the method of forming is forming by metal mold pressing, then the ratio of the basalt fibers to the binder is 7:3, or close to 7:3 within a specified tolerance. The term "specified tolerance" means that a specified error range may be set, e.g. within ±5%. The error range may be specified manually according to the application scenario of the medical apparatus member or bed board used.

Third Embodiment: Forming by Vacuum Infusion Low-Pressure Forming (RTM)

If the method of forming is by RTM, then when the pressure is lower than a specified pressure, the ratio of the basalt fibers to the binder is 6:4, or close to 6:4 within a specified tolerance; when the pressure is increased, the proportion of the basalt fibers also synchronously increases by a specified value. The specified pressure may be specified manually according to the specific application scenario. The term "specified tolerance" means that a specified error range may be set, e.g. within ±5%. The error range may be specified manually according to the application scenario of the medical apparatus member or bed board used. In other words, when the third embodiment is used, in the case where the pressure is low, the ratio of the basalt fibers to the binder is 6:4, or close to 6:4 within a specified tolerance; when the pressure increases by one level, the proportion of basalt fibers also correspondingly increases by one level, e.g. the ratio of the basalt fibers to the binder is 7:3, or close to 7:3 within a specified tolerance; if the pressure increases further, then the proportion of basalt fibers increases further correspondingly.

With regard to the structure of the member or bed board, this may be a structure based on actual needs, e.g. a cuboid, plate-like, columnar or T-shaped. A member or bed board with a corresponding structure is made by mixing and forming basalt fibers and binder.

In another preferred embodiment of the medical apparatus member or bed board, the medical apparatus member or bed board has a shell and a lightweight filler. The shell is made by binding basalt fibers with a binder in a specified ratio; the interior of the shell is hollow, and filled with the lightweight filler.

In an embodiment of a diagnostic bed for a medical apparatus, the bed board comprises a shell and a lightweight filler. The shell is made by binding basalt fibers with a binder in a specified ratio; the interior of the shell is hollow, and filled with the lightweight filler.

Corresponding to the embodiment of the medical apparatus member or bed board, the present invention also encompasses a method for manufacturing a member or bed board for a medical apparatus, the method principally comprising: using basalt fibers and an adhesive in a specified ratio to make a shell, using the shell to enclose a filler, and forming the member or bed board for the medical apparatus.

In a preferred embodiment, the filler is any of the following substances: wood-based material, foamed material, plastic, etc. The foamed material may for example specifically be polymethacrylimide (PMI) foamed material or polyurethane (PU) foamed material, etc.

The shell may specifically be formed from basalt fibers and a binder in a specified ratio by any of the following embodiments.

First Embodiment: Forming by Manual Pasting

If the method of forming is forming by manual pasting, then the ratio of the basalt fibers to the binder is 1:1, or close to 1:1 within a specified tolerance. The term "specified tolerance" means that a specified error range may be set, e.g. within ±5%. The error range may be specified manually according to the application scenario of the medical apparatus member or bed board used.

Second Embodiment: Framing by Metal Mold Pressing

This method of processing has the advantage of high efficiency. If the method of forming is forming by metal mold pressing, then the ratio of the basalt fibers to the binder is 7:3, or close to 7:3 within a specified tolerance. The term "specified tolerance" means that a specified error range may be set, e.g. within ±5%. The error range may be specified manually according to the application scenario of the medical apparatus member or bed board used.

Third Embodiment: Forming by Vacuum Infusion Low-Pressure Forming (RTM)

If the method of forming is by RTM, then when the pressure is lower than a specified pressure, the ratio of the basalt fibers to the binder is 6:4, or close to 6:4 within a specified tolerance; when the pressure is increased, the proportion of the basalt fibers also synchronously increases by a specified value. The specified pressure may be specified manually according to the specific application scenario. The term "specified tolerance" means that a specified error range may be set, e.g. within ±5%. The error range may be specified manually according to the application scenario of the medical apparatus member or bed board used. In other words, when the third embodiment is used, in the case where the pressure is low, the ratio of the basalt fibers to the binder is 6:4, or close to 6:4 within a specified tolerance; when the pressure increases by one level, the proportion of basalt fibers also correspondingly increases by one level, e.g. the ratio of the basalt fibers to the binder is 7:3, or close to 7:3 within a specified tolerance; if the pressure increases further, then the proportion of basalt fibers increases further correspondingly.

A member for a medical apparatus, such as a bed board for a medical apparatus, that is formed by adding a filler in this way, has the following advantages:

(1) the bed board is simple to make, and pre-embedding in the interior is possible;

(2) it is easily connected to a metal component;

(3) it is light in weight.

In particular, in a scenario in which the member or bed board for a medical apparatus according to the present invention is used in a CT bed board or C-arm bed board, it may be used together with a filler, i.e. the method of the embodiment described above may be employed, i.e. basalt fibers enclose the filler, and the bed board for the medical apparatus is formed. A bed board made in this way has good adhesion, image quality and image noise fully meet the service requirements, the problem of the use of a single material in medical apparatuses is solved, and the substitutability of basalt fibers is achieved. Moreover, components with anti-bending requirements, support plates, and supports that are not subject to stringent precision requirements may be replaced. In other words, these components with anti-bending requirements, support plates, and supports that are not subject to stringent precision requirements may also be made using the member for a medical apparatus according to the present invention.

In summary, the present invention applies a new material, namely basalt fibers, in a medical apparatus member. Basalt fibers have excellent properties such as being lightweight, acid-resistant, alkali-resistant, insulating, anti-magnetic, high temperature resistant and fire resistant, and having a high tensile strength (6-10 times that of a metal material), and are suitable for use in a medical apparatus member such as a bed board. Basalt fiber material can increase the overall rigidity of a bed board, and unexpectedly, when the medical apparatus member having basalt fibers according to the present invention is used, the quality of medical apparatus scanned images will also be vastly improved. In particular, in MR bed board applications, test results show that image quality is superior to that of fiberglass and other non-metallic materials, and mold pressing in a single operation is possible. In CT bed board and C-Arm bed board applications, to reduce weight and cost, basalt fibers may be used together with a filler, and adhesion is good, image quality and image noise fully meet the service requirements, the problem of the use of a single material in medical apparatuses is solved, and the substitutability of basalt fibers is achieved.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for manufacturing a bed board, comprising:
    forming a bed board body from basalt fibers and a binder in a predetermined ratio, and to give said bed board body a size and shape that fit within a medical imaging apparatus selected from the group consisting of a magnetic resonance imaging apparatus and an x-ray imaging apparatus;
    forming said bed board by a procedure selected from the group consisting of manual pasting, metal mold pressing, and vacuum infusion low-pressure forming;
    when said bed board is formed by said manual pasting, using, as said predetermined ratio, a ratio of the basalt fibers to the binder that is 1:1;
    when said bed board is formed by said metal mold pressing, using, as said predetermined ratio, a ratio of the basalt fibers to the binder that is 7:3; and
    when said bed board is formed by said vacuum infusion low-pressure forming, using, as said predetermined ratio, a ratio of the basalt fibers to the binder that is 6:4.

2. A method as claimed in claim 1 comprising, when said bed board is firmed by said vacuum infusion low-pressure forming, selecting a value for said pressure, and increasing a proportion of said basalt fibers in said ratio synchronously as the selected pressure approaches said predetermined pressure.

* * * * *